(12) United States Patent
Eriksson et al.

(10) Patent No.: US 7,345,063 B2
(45) Date of Patent: Mar. 18, 2008

(54) AMIDES, PREPARATION AND THERAPEUTIC USE AS MODULATORS OF CCR-RECEPTOR ACTIVITY

(75) Inventors: Tomas Eriksson, Lund (SE); Karolina Lawitz, Lund (SE)

(73) Assignee: AstraZeneca AB (SE)

( * ) Notice: Subject to any disclaimer, the term of this patent is extended or adjusted under 35 U.S.C. 154(b) by 343 days.

(21) Appl. No.: 10/472,017

(22) PCT Filed: Mar. 19, 2002

(86) PCT No.: PCT/SE02/00541

§ 371 (c)(1),
(2), (4) Date: Jan. 8, 2004

(87) PCT Pub. No.: WO02/076457

PCT Pub. Date: Oct. 3, 2002

(65) Prior Publication Data

US 2004/0122020 A1 Jun. 24, 2004

(30) Foreign Application Priority Data

Mar. 23, 2001 (SE) .................................. 0101038

(51) Int. Cl.
*A61K 31/4439* (2006.01)
*C07D 401/12* (2006.01)

(52) U.S. Cl. .................. 514/343; 546/278.4
(58) Field of Classification Search ............. 546/278.4; 514/343
See application file for complete search history.

(56) References Cited

U.S. PATENT DOCUMENTS

| | | |
|---|---|---|
| 3,203,992 | 8/1965 | Kunz et al. |
| 3,577,432 | 5/1971 | Helsley et al. |
| 3,755,584 | 8/1973 | Plotnikoff et al. |
| 3,818,017 | 6/1974 | Janssen et al. |
| 3,894,030 | 7/1975 | Janssen et al. |
| 4,029,801 | 6/1977 | Cavalla et al. |
| 4,080,328 | 3/1978 | Maruyama et al. |
| 4,166,119 | 8/1979 | Effland et al. |
| 4,264,613 | 4/1981 | Regnier et al. |
| 4,304,915 | 12/1981 | Berthold |
| 4,338,323 | 7/1982 | Regnier et al. |
| 5,576,321 | 11/1996 | Krushinski, Jr. et al. |
| 5,614,523 | 3/1997 | Audia et al. |
| 5,614,533 | 3/1997 | Anderson et al. |
| 5,627,196 | 5/1997 | Audia et al. |
| 5,741,789 | 4/1998 | Hibschman et al. |
| 5,789,402 | 8/1998 | Audia et al. |

FOREIGN PATENT DOCUMENTS

| | | |
|---|---|---|
| DE | 37 23 568 | 1/1989 |
| DE | 37 23 648 | 1/1989 |
| DE | 197 03 131 | 7/1998 |
| DE | 197 55 268 | 6/1999 |
| EP | 0 095 454 | 11/1983 |
| EP | 0 128 007 | 12/1984 |
| EP | 0 496 691 | 7/1992 |
| EP | 0 587 311 | 3/1994 |
| EP | 0 722 941 | 7/1996 |
| EP | 0 903 349 | 3/1999 |
| FR | 2 190 430 | 2/1974 |
| GB | 1368012 | 9/1974 |
| WO | WO93/25528 | 12/1993 |
| WO | WO97/23458 | 7/1997 |
| WO | WO98/32442 | 7/1998 |
| WO | WO99/25686 | 5/1999 |
| WO | WO99/31092 | 6/1999 |
| WO | WO99/65895 | 12/1999 |
| WO | WO 00/35449 | 6/2000 |
| WO | WO 00/35451 | 6/2000 |
| WO | WO 00/53600 | 9/2000 |
| WO | WO 00/58305 | 10/2000 |
| WO | WO 00/69820 | 11/2000 |
| WO | WO 01/14333 | 3/2001 |
| WO | WO 01/43744 | 6/2001 |
| WO | WO 01/44227 | 6/2001 |
| WO | WO 01/87839 | 11/2001 |

OTHER PUBLICATIONS

Barnes et al., "Prospects fornew drugs, etc.," Lancet 2004; 364, pp. 985-996.*
Barnes, "COPD: is there light at the end of the tunnel?", Current Opinion in Pharmacology 2004, 4: 263-272.*
de Boer, "Potential new drugs for therapy, etc.," Expert. Opin. Investig. Drugs (2003) 12(7): 1067-1086.*
U.S. Appl. No. 10/204,754, filed Aug. 23, 2002, Hansen et al.
U.S. Appl. No. 10/204,789, filed Aug. 23, 2002, Hansen et al.
U.S. Appl. No. 10/204,790, filed Aug. 23, 2002, Bodkin et al.
U.S. Appl. No. 10/311,667, filed Dec. 17, 2002, Eriksson et al.
U.S. Appl. No. 10/311,841, filed Dec. 17, 2002, Eriksson et al.
U.S. Appl. No. 10/468,179, filed Aug. 18, 2003, Brough et al.
U.S. Appl. No. 10/472,412, filed Sep. 16, 2003, Eriksson et al.
Archibald et al., "Antiinflammatory 4-acylaminopiperidines", *CAPLUS* 77:34355 (1972).
Cattanach et al., "Studies in the Indole Series. Part IV. Tetrahydro-1*H*-pyrido[4, 3-b]-indoles as Serotonin Antagonists", *J. Chem. Soc.* C. 10:1235-1243 (1968).
Cohen et al., "Cytokine function: A study in biologic diversity", *CAPLUS* 125:31527 (1996).

(Continued)

*Primary Examiner*—Patricia L. Morris
(74) *Attorney, Agent, or Firm*—Fish & Richardson P.C.

(57) ABSTRACT

The invention provides compounds of general formula (I), wherein $R^1$, X, Y, n, $R^2$, $Z^1$, $Z^2$, $A^1$, $A^2$, Q, $R^3$, $R^4$, $R^5$, $R^6$, $R^7$, $R^8$, t and $R^{16}$ are as defined in the specification, processes for their preparation, pharmaceutical compositions containing them and their use in therapy (I)

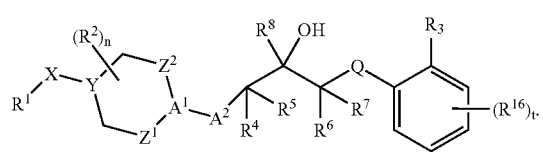

8 Claims, No Drawings

OTHER PUBLICATIONS

Friebe et al., "Piperidinopropyl derivatives and pharmaceutical compositions containing them", *CAPLUS* 94:103172 (1981).

Hesselgesser et al., "Identification and Characterization of Small Molecule Functional Antagonists of the CCR1 Chemokine Receptor", *J. Biol. Chem.* 273(25):15687-15692 (1998).

Howard et al., "Chemokines: progress toward identifying molecular targets for therapeutic agents", *Trends in Biotechnology* 14:46-51 (1996).

Manabu Hori Kim D. Janda, "A Soluble Polymer Approach to the "Fishing Out" Principle: Synthesis and Purification of β-Amino Alcohols", *J. Org. Chem.* 63:889-894 (1998).

Komai et al., "Structure-Activity Relationships of HIV-1 PR Inhibitors Containing AHPBA-II. Modification of Pyrrolidine Ring at P1' Proline", *Bioorganic & Medicinal Chemistry* 4(8):1365-1377 (1996).

Leclerc et al., "Derivatives Related to Betaxolol with I-and J-Adrenergic Activities", *Arzneim.-Forsch/Drug. Res.* 35(11):1357-1367 (1985).

Meurer et al., "Discovery of potent human CCR5 antagonists for the treatment of HIV-1 infection—II.", *CAPLUS* 2000:331722 (2000).

Navas III et al., "The Design and Synthesis of a Hapten for 1192U90, A Potential Atypical Antipsychotic Agent", *Synthetic Communications* 26(7):1411-1421 (1996).

Payard et al., "N-Aminomethylated Derivatives of Some Hydroxamic Acids as Anti-Inflammatories", *Eur. J. Med. Chem.* pp. 1-10 (1975).

Rubini et al., "Synthesis of Isosteric Methylene-Oxy Pseudodipeptide Analogues as Novel Amide Bond Surrogate Units", *Tetrahedron* 42(21):6039-6045 (1986).

STN Int'l, *CAPLUS* 1968.402884.

Timmermans et al., "Hypotensive Properties of Benzodioxane Derivatives Structurally Related to R 28935. Comparison of Activity with some Receptor Affinities", *Arch. int. Pharmacodyn.* 255:321-334 (1982).

Wright et al., "Discovery of Selective Dopamine D4 Receptor Antagonists: 1-Aryloxy-3-(4-Aryloxypiperidinyl)-2-Propanols", *Bioorganic & Medicinal Chemistry Letters* 7(11):1377-1380 (1997).

Alcaraz et al., "Preparation of piperidinyl alcohols as chemokine receptor modulators for treatment of diseases such as asthma", *CAPLUS* 139:197375 (2003).

Bechtloff et al., "Pseudopolymorphs in industrial use", *SciSearch* 10289666 (2001).

Berthold, "3-Aminopropoxyaryl derivatives", *CAPLUS* 93:8015 (1980).

Black et al., "Increased chemical purity using a hydrate", *SciSearch* 12765805 (2004).

Chou et al., "Adrenergic regulation of macrophage-derived tumor necrosis factor-α generation during a chronic polyarthritus pain model", *CAPLUS* 129:3784 (1998).

Eriksson et al., "Preparation of benzimidazol derivatives as modulators of chemokine receptors", *CAPLUS* 137:2476987 (2002).

Exhibit A CAS search result.

Hu et al., "Dependence of the chemical dynamics of intercluster association reactions on the strength of the solute-solvent intermolecular potential", *Beilstein Abs.* 5809171 (1993).

Katritsky et al., "Heterocyclic Chemistry", Cambridge, p. 75 (1964).

Levine, "β2-Andrenergic mechanisms in experimental arthritis", *CAPLUS* 109:25680 (1988).

Matsuo et al., "Preparation of N-pentadienoylaminoalkyl-4-(3-indolyl) piperidines and analogs as antiallergic agents", *CAPLUS* 155:232091 (1991).

Mizuhashi, "A guinea pig model of propranolol-induced bronchoconstriction (PIB) after allergic immediate asthmatic reaction and the role of thromboxane A2 and 5-lipoxygenase products", *CAPLUS* 122:717129 (1995).

Saeki, "Moleclar mechanism of rheumatoid arthrutus and relationship between cytokine and chronic rheumatoid arthritus", *CAPLUS* 125:272100 (1996).

Schmidt et l., "Molecular mechanism in allergy and clinical immunology", *J Allergy Clin Immunol* 105:673-682 (2000).

Tanabe et al., "Propanol derivatives as antihypertensives", *CAPLUS* 96:110143 (1982).

Tanaka et al., "Antiallergic effects of a novel compound, SWR-00151", *CAPLUS* 126:311929 (1997).

Wright et al., "Subtype-Selective N-Methyl-D-Aspartate Receptor Antagonists: Synthesis and Biological Evaluation of 1-(Heteroarylalkynl)-4-benzylpiperidines", *CAPLUS* 133:321781 (2000).

Yamamoto, "Expression of monocyte chemotactic by cross-linked dimerization of a ribosomal protein", *CAPLUS* 127::64176 (1997).

Zenitz et al., "3-(Piperidino-lower-alkyl) indoles", *CAPLUS* 87:102164 (1977).

* cited by examiner

AMIDES, PREPARATION AND THERAPEUTIC USE AS MODULATORS OF CCR-RECEPTOR ACTIVITY

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small Secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemolines include several potent chemoattractants and activators of neutrophils such as interleulin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those previously mentioned.

In accordance with the present invention, there is therefore provided a compound of general formula

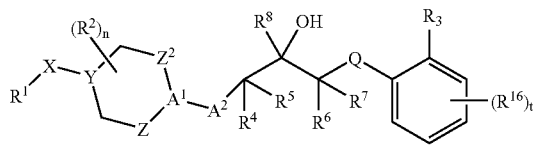

(I)

wherein
- $R^1$ represents a saturated or unsaturated 5- to 10-membered heterocyclic ring system comprising at least one ring heteroatom selected from nitrogen, oxygen and sulphur, the ring system being optionally substituted by one or more substituents independently selected from halogen, cyano, nitro, carboxyl, hydroxyl, $C_1$-$C_6$ alkyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido (—$SO_2NH_2$), $C_1$-$C_6$ alkylsulphonyl and —$C(O)NR^{11}R^{12}$;
- X represents an oxygen or sulphur atom or a $CH_2$, $CH(CH_3)$, $OCH_2$, $CH_2O$, $CH_2NH$, NH or carbonyl group and Y represents a nitrogen atom or a CH or C(OH) group, provided that when X represents an oxygen or sulphur atom or a $CH_2O$, $CH_2NH$ or NH group, then Y represents a CH group;
- n is 0, 1 or 2;
- each $R^2$ independently represents a $C_1$-$C_6$ alkyl, $C_1$-$C_6$ alkoxycarbonyl, —$CH_2OH$ or carboxyl group;
- $Z^1$ represents a bond or a group $(CH_2)_q$ where q is 1 or 2;
- $Z^2$ represents a bond or a group $CH_2$, with the proviso that $Z^1$ and $Z^2$ do not both simultaneously represent a bond;
- when Y represents a nitrogen atom, then $A^1$ represents CH and $A^2$ represents NH, or $A^1$ represents a nitrogen atom and $A^2$ represents $CH_2$, or $A^1$ represents a nitrogen atom and $A^2$ represents a bond; or when Y represents a group CH or C(OH), then $A^1$ represents a nitrogen atom and $A^2$ represents a bond;
- Q represents an oxygen or sulphur atom or a group $CH_2$ or NH;
- $R^3$ represents —$NHC(O)R^{13}$ or —$C(O)NR^{14}R^{15}$;
- $R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;
- $R^8$ represents a hydrogen atom, a $C_1$-$C_6$ alkyl group or is linked to $R^4$ as defined above;
- $R^9$ and $R^{10}$ each independently represent a hydrogen atom or a $C_1$-$C_6$ alkyl group, or $R^9$ and $R^{10}$ together with the nitrogen atom to which they are attached form a 4- to 7-membered saturated heterocycle;
- $R^{11}$ and $R^{12}$ each independently represent a hydrogen atom or a $C_1$-$C_6$ alkyl group;
- $R^{13}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one ring heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —$NHC(O)$—$R^{17}$;
- $R^{14}$ and $R^{15}$ each independently represent (i) a hydrogen atom, (ii) a 5- to 6-membered saturated or unsaturated ring optionally comprising at least one ring heteroatom selected from nitrogen, oxygen and sulphur, the ring being optionally substituted with at least one substituent selected from halogen, methyl and trifluoromethyl, or (iii) a $C_1$-$C_6$ alkyl group optionally substituted by at least one substituent selected from halogen, trifluoromethyl, carboxyl, $C_1$-$C_6$ alkoxycarbonyl and a 5- to 6-membered saturated or unsaturated ring optionally comprising at least one ring heteroatom selected from nitrogen, oxygen and sulphur, the ring being optionally substituted with at least one substituent selected from halogen, methyl and trifluoromethyl, or
- $R^{14}$ and $R^{15}$ together with the nitrogen atom to which they are attached form a 4- to 7-membered saturated heterocycle;
- t is 0, 1, 2 or 3;
- each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —NR$^{18}$R$^{19}$, C$_3$-C$_6$ cycloalkylamino, C$_1$-C$_6$ alkylthio, C$_1$-C$_6$ alkylcarbonyl, C$_1$-C$_6$ alkylcarbonylamino, sulphonamido (—SO$_2$NH$_2$), C$_1$-C$_6$ alkylsulphonyl, —C(O)NR$^{20}$R$^{21}$, —NR$^{22}$C(O)(NH)$_v$R$^{23}$, phenyl, or C$_1$-C$_6$ alkyl optionally substituted by at least one substituent selected from carboxyl and C$_1$-C$_6$ alkoxycarbonyl;

R$^{17}$ represents a C$_1$-C$_6$ alkyl, amino (—NH$_2$) or phenyl group;

R$^{18}$ and R$^{19}$ each independently represent a hydrogen atom or a C$_1$-C$_6$ alkyl group, or R$^{18}$ and R$^{19}$ together with the nitrogen atom to which they are attached form a 4- to 7-membered saturated heterocycle;

R$^{20}$ and R$^{21}$ each independently represent a hydrogen atom or a C$_1$-C$_6$ alkyl group optionally substituted by C$_1$-C$_6$ alkoxycarbonyl;

v is 0 or 1;

R$^{22}$ represents a hydrogen atom or a C$_1$-C$_6$ alkyl group; and

R$^{23}$ represents a hydrogen atom, or a C$_1$-C$_6$ alkyl group optionally substituted by at least one substituent selected from carboxyl, C$_1$-C$_6$ alkoxy and C$_1$-C$_6$ alkoxycarbonyl; or a pharmaceutically a(eptable sait or solvate thereof.

In the context of the present specification, an alkyl or alkenyl substituent group or an alkyl moiety in a substituent group may be linear or branched. A haloalkyl or haloalkoxy substituent group will comprise at least one halogen atom, e.g. one, two, three or four halogen atoms. When R$^9$ and R$^{10}$ (or R$^{14}$ and R$^{15}$, or R$^{18}$ and R$^{19}$) represent a 4- to 7-membered saturated heterocycle, it should be understood that the only heteroatom present is the nitrogen atom to which R$^9$ and R$^{10}$ (or R$^{14}$ and R$^{15}$, or R$^{18}$ and R$^{19}$) are attached. In the definitions of each of R$^1$ and R$^{13}$, it should be noted that the saturated or unsaturated 5- to 10-membered heterocyclic ring system may have alicyclic or aromatic properties.

Similarly, in the definition of R$^{14}$ and R$^{15}$, a 5- to 6-membered saturated or unsaturated ring optionally comprising at least one ring heteroatom may have alicyclic or aromatic properties.

R$^1$ represents a saturated or unsaturated 5- to 10-membered heterocyclic ring system comprising at least one ring heteroatom (e.g. one, two, three or four ring heteroatoms) selected from nitrogen, oxygen and sulphur, the ring system being optionally substituted by one or more (e.g. one, two, three or four) substituents independently selected from halogen (e.g. chlorine, fluorine, bromine or iodine), cyano, nitro, carboxyl, hydroxyl, C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_3$-C$_6$ cycloalkyl (cyclopropyl, cyclobutyl, cyclopentyl or cyclohexyl), C$_1$-C$_6$, preferably C$_1$-C$_4$, alkoxy (e.g. methoxy, ethoxy, n-propoxy or n-butoxy), C$_1$-C$_6$, preferably C$_1$-C$_4$, alkoxycarbonyl (e.g. methoxycarbonyl or ethoxycarbonyl), C$_1$-C$_6$, preferably C$_1$-C$_4$, haloalllyl (e.g. trifluoromethyl), C$_1$-C$_6$, preferably C$_1$-C$_4$, haloalkoxy (e.g. trifluoromethoxy), —NR$^9$R$^{10}$, C$_3$-C$_6$ cycloalkylamino (e.g. cyclopropylamino, cyclobutylamino, cyclopentylamino or cyclohexylamino), C$_1$-C$_6$, preferably C$_1$-C$_4$, alkylthio (e.g. methylthio or ethylthio), C$_1$-C$_6$, preferably C$_1$-C$_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), C$_1$-C$_6$, preferably C$_1$-C$_4$, alkylcarbonylamino (e.g. methylcarbonylamino or ethylcarbonylamino), sulphonamido, C$_1$-C$_6$, preferably C$_1$-C$_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl) or —C(O)NR$^{11}$R$^{12}$.

The saturated or unsaturated 5- to 10-membered heterocyclic ring system may be monocyclic or polycyclic (e.g. bicyclic) and comprises up to four ring heteroatoms independently selected fiom nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

In an embodiment of the invention, R$^1$ represents an unsaturated 5- to 6-membered heterocyclic ring system comprising at least one ring nitrogen atom, the ring system being optionally substituted by one or more halogen atoms.

In an embodiment of the invention, X represents an oxygen atom or a CH$_2$, OCH$_2$, CH$_2$O, NH or carbonyl group.

In another embodiment of the invention, Y represents a nitrogen atom or CH group.

Preferred combinations of X—Y include O—CH, OCH$_2$—CH, NH—CH, CH$_2$O—CH, CH$_2$—N, C(O)—N and CH$_2$—CH.

Preferred combinations of Y, Z$^1$ and Z$^2$ include:

| Y | Z$^1$ | Z$^2$ |
|---|---|---|
| CH | CH$_2$ | bond |
| CH | bond | CH$_2$ |
| CH | CH$_2$ | CH$_2$ |
| CH | (CH$_2$)$_2$ | bond |
| N | CH$_2$ | CH$_2$ |

Each R$^2$ independently represents a C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_1$-C$_6$, preferably C$_1$-C$_4$, alkoxycarbonyl (e.g. methoxycarbonyl or ethoxycarbonyl), —CH$_2$OH or carboxyl group. In an embodiment of the invention, n is 1 and R$^2$ represents a methyl, methoxycarbonyl, ethoxycarbonyl, —CH$_2$OH or carboxyl group.

In an embodiment of the invention, Q represents an oxygen atom.

R$^4$, R$^5$, R$^6$ and R$^7$ each independently represent a hydrogen atom or a C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), or R$^4$, R$^5$, R$^6$ and R$^7$ together represent a C$_1$-C$_4$ alkylene chain linking the two carbon atoms to which they are attached to form a 4- to 7-membered saturated carbocycle (e.g. cyclopentyl or cyclohexyl), or R$^5$, R$^6$ and R$^7$ each represent a hydrogen atom and R$^4$ and R$^8$ together with the carbon atoms to which they are attached form a 5- to 6-membered saturated carbocycle (particularly cyclopentyl).

R$^8$ represents a hydrogen atom, a C$_1$-C$_6$, preferably C$_1$-C$_4$, alkyl group (e.g. methyl, ethyl, n-propyl, isopropyl, n-butyl, isobutyl, tert-butyl, n-pentyl or n-hexyl) or is linked to R$^4$ as defined above.

R$^9$ and R$^{10}$ each independently represent a hydrogen atom or a C$_1$-C$_6$, preferably C$_1$-C$_4$, alkyl group (e.g. methyl, ethyl, n-propyl, isopropyl, n-butyl, isobutyl, tert-butyl, n-pentyl or n-hexyl), or R$^9$ and R$^{10}$ together with the nitrogen atom to which they are attached form a 4- to 7-membered saturated heterocycle (e.g. pyrrolidinyl or piperidinyl).

$R^{11}$ and $R^{12}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

$R^{13}$ represents a group $C_1$-$C_6$, preferably $C_1$-$C_5$, alkyl group (e.g. methyl, ethyl, n-propyl, isopropyl, n-butyl, isobutyl, tert-butyl, n-pentyl or n-hexyl), $C_2$-$C_6$, preferably $C_2$-$C_4$, alkenyl, $C_3$-$C_6$ cycloalkyl (cyclopropyl, cyclobutyl, cyclopentyl or cyclohexyl), adamantyl, $C_5$-$C_6$ cycloalkenyl, phenyl or a saturated or unsaturated 5- to 10-membered heterocyclic ring system comprising at least one ring heteroatom (e.g. one, two, three or four ring heteroatoms) selected from nitrogen, oxygen and sulphur, each of which (i.e. each of the recited groups and the ring system) may be optionally substituted by one or more (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—$R^{17}$.

In $R^{13}$, the saturated or unsaturated 5- to 10-membered heterocyclic ring system may be monocyclic or polycyclic (e.g. bicyclic) and comprises up to four ring heteroatoms independently selected from nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

In an embodiment of the invention, $R^{13}$ represents a group $C_1$-$C_6$ alkyl, phenyl or a saturated or unsaturated 5- to 6-membered heterocyclic ring system comprising at least one ring heteroatom (e.g. one or two ring heteroatoms independently) selected from nitrogen, oxygen and sulphur, each of which may be optionally substituted by one, two, three or four substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$.

In another embodiment of the invention, $R^{13}$ represents a group $C_1$-$C_6$ alkyl, phenyl or an unsaturated 5- to 6-membered heterocyclic ring system comprising at least one ring heteroatom (e.g. one or two ring heteroatoms independently) selected from nitrogen and oxygen, each of which may be optionally substituted by one or two substituents independently selected from halogen, $C_1$-$C_6$ alkyl and $C_1$-$C_6$ alkoxy.

$R^{14}$ and $R^{15}$ each independently represent (i) a hydrogen atom, (ii) a 5- to 6-membered saturated or unsaturated ring optionally comprising at least one ring heteroatom (e.g. one, two or three ring heteroatoms independently) selected from nitrogen, oxygen and sulphur (examples of rings include cyclopentyl, cyclohexyl, pyrolyl, imidazolyl, pyridinyl, pyrazinyl, pyridazinyl, pyrimidinyl, thienyl and furanyl), the ring being optionally substituted with at least one substituent (e.g. one, two or three substituents independently) selected from halogen (e.g. fluorine, chlorine, bromine or iodine), methyl and trifluoromethyl, or (iii) a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from halogen (e.g. fluorine, chlorine, bromine or iodine), trifluoromethyl, carboxyl, $C_1$-$C_6$, preferably $C_1$-$C_4$, alkoxycarbonyl and a 5- to 6-membered saturated or unsaturated ring optionally comprising at least one ring heteroatom (e.g. one, two or three ring heteroatoms independently) selected from nitrogen, oxygen and sulphur (examples of rings include cyclopentyl, cyclohexyl, pyrolyl, imidazolyl, pyridinyl, pyrazinyl, pyridazinyl, pyrimidinyl, thienyl and furanyl), the ring being optionally substituted with at least one substituent (e.g. one, two or three substituents independently) selected from halogen (e.g. fluorine, chlorine, bromine or iodine), methyl and trifluoromethyl, or $R^{14}$ and $R^{15}$ together with the nitrogen atom to which they are attached form a 4- to 7-membered saturated heterocycle (e.g. pyrrolidinyl or piperidinyl).

In an embodiment of the invention, $R^{14}$ and $R^{15}$ each independently represent a hydrogen atom or an unsubstituted $C_1$-$C_6$ alkyl group.

Each $R^{16}$ independently represents halogen (e.g. chlorine, fluorine, bromine or iodine), cyano, nitro, carboxyl, hydroxyl, $C_3$-$C_6$ cycloalkyl (cyclopropyl, cyclobutyl, cyclopentyl or cyclohexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl or ethoxycarbonyl), $C_1$-$C_6$, preferably $C_1$-$C_4$, haloalkyl (e.g. trifluoromethyl), $C_1$-$C_6$, preferably $C_1$-$C_4$, haloalkoxy (e.g. trifluoromethoxy), —$NR^{18}R^{19}$, $C_3$-$C_6$ cycloalkylamino (e.g. cyclopropylamino, cyclobutylamino, cyclopentylamino or cyclohexylamino), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkylcarbonylamino (e.g. methylcarbonylamino or ethylcarbonylamino), sulphonamido, $C_1$-$C_6$, preferably $C_1$-$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^{20}R^{21}$, —$NR^{22}C(O)$—$(NH)_xR^{23}$, phenyl, or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents) independently selected from carboxyl and $C_1$-$C_6$, preferably $C_1$-$C_4$, alkoxycarbonyl (e.g. methoxycarbonyl or ethoxycarbonyl).

In an embodiment of the invention, each $R^{16}$ independently represents halogen, hydroxyl, cyano, $C_1$-$C_4$ alkoxy, $C_1$-$C_4$ alkoxycarbonyl, $C_1$-$C_4$ haloalkyl, $C_1$-$C_4$ alkylcarbonyl, phenyl or $C_1$-$C_4$ alkyl.

$R^{17}$ represents a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), amino or phenyl group.

$R^{18}$ and $R^{19}$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), or $R^{18}$ and $R^{19}$ together with the nitrogen atom to which they are attached form a 4- to 7-membered saturated heterocycle (e.g. pyrrolidinyl or piperidinyl).

$R^{20}$ and $R^{21}$ each independently represent a hydrogen atom or a $C_1$-$C_6$, preferably $C_{1-4}$, alkyl group (e.g. methyl, ethyl, n-propyl, isopropyl, n-butyl, isobutyl, tert-butyl, n-pentyl or n-hexyl) optionally substituted by a $C_1$-$C_6$, preferably $C_1$-$C_4$, alkoxycarbonyl substituent group.

$R^{22}$ represents a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

$R^{23}$ represents a hydrogen atom, or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from carboxyl, $C_1$-$C_6$, preferably $C_1$-$C_4$, alkoxy or $C_1$-$C_6$, preferably $C_1$-$C_4$, alkoxycarbonyl.

Examples of compounds of the invention include:
N-[2-(3-(3-[(5-Chloro-2-pyridinyl)oxy]-1-pyrrolidinyl)-2-hydroxypropoxy) phenyl]benzamide,
N-[2-(3-{3-[(5-Chloro-2-pyridinyl)oxy)]-1-pyrrolidinyl}-2-hydroxypropoxy}-6-fluorophenyl]acetamide,
N-[2-(3-(3-[(5-Chloro-2-pyridinyl)oxy]-1-pyrrolidinyl)-2-hydroxypropoxy)-phenyl]acetamide
N-[2-[(2S)-3-(3-[(5-Chloro-2-pyridinyl)oxy]-1-pyrrolidinyl)-2-hydroxypropoxy)-4-fluorophenyl]acetamide,
N-[2-[(2R)-3-(3-[(5-Chloro-2-pyridinyl)oxy-]1-pyrrolidinyl)-2-hydroxypropoxy)-4-fluorophenyl]acetamide,
N-[2-(3-(3-[(5-Chloro-2-pyridinyl)oxy]-1-pyrrolidinyl)-2-hydroxypropoxy)-phenyl]3,5-dimethyl-1H-pyrrole-2-carboxyamide,
N-[2-(3-(3-[(6-Chloro-2-pyridinyl)oxy]-1-pyrrolidinyl)-2-hydroxypropoxy) phenyl]benzamide,
N-[2-[(2S)-3-3-[(6-Chloro-2-pyridinyl)oxy]-1-pyrrolidinyl)-2-hydroxypropoxy)-4-fluorophenyl]acetamide,
N-[2-3-(3-[(5-Bromo-2-pyridinyl)oxy]-1-pyrrolidinyl)-2-hydroxypropoxy)phenyl]benzamide,
N-[2-(3-(3-[(5-Bromo-2-pyridinyl)oxy]-1-pyrrolidinyl)-2-hydroxypropoxy)-6-fluoroph enyl]acetamide,
N-[2-(3-(3-[(5-Bromo-2-pyridinyl)oxy]-1-pyrrolidinyl)-2-hydroxypropoxy)phenyl]acetamide,
N-[2-[(2S)-3-(3-[(5-Bromo-2-pyridinyl)oxy]-1-pyrrolidinyl)-2-hydroxypropoxy)-4-fluorophenyl]acetamide,
N-[2-[(2R)-3-(3-[(5-Bromo-2-pyridinyl)oxy]-1-pyrrolidinyl)-2-hydroxypropoxy)-4-fluorophenyl]acetamide,
N-[2-(3-(3-[(5-Bromo-2-pyridinyl)oxy]-1-pyrrolidinyl)-2-hydroxypropoxy)-phenyl]-3,5-diethyl-1H-pyffole-2-carboxyamide,
N-[2-(2-Hydroxy-3-{3-[(4-methyl-2-pyridinyl)oxy]-1-pyrrolidinyl}propoxy) phenylbenzamide, and
N-{4-Fluoro-2-[((2S)2-hydroxy-3-{3-[(4-methyl-2-pyridinyl)oxy]-1-pyrrolidinyl}propyl)oxy] phenyl}acetamide.

The present invention further provides a process for the preparation of a compound of formula (I) as defined above which comprises,
(a) reacting either a compound of general formula

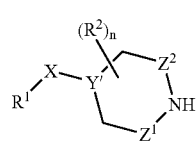
(II)

wherein Y' represents CH or C(OH) and $R^1$, X, n, $R^2$, $Z^1$ and $Z^2$ are as defined in formula (I), or a compound of general formula

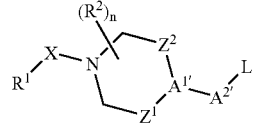
(II')

wherein $A^{1'}$ represents CH and $A^{2'}$ represents NH, or $A^{1'}$ represents a nitrogen atom and $A^{2'}$ represents $CH_2$ or a bond, L represents a hydrogen atom or an activating group (e.g. Li) and $R^1$, X, n, $R^2$, $Z^1$ and $Z^2$ are as defined in formula (I), with a compound of general formula

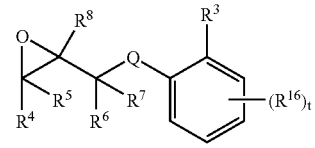
(III)

wherein Q, $R^3$, $R^4$, $R^5$, $R^6$, $R^7$, $R^8$, t and $R^{16}$ are as defined in formula (I); or (b) reacting a compound of general formula

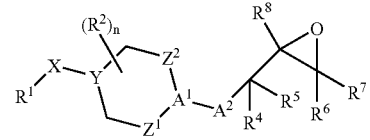
(IV)

wherein $R^1$, X, Y, n, $R^2$, $Z^1$, $Z^2$, $A^1$, $A^2$, $R^4$, $R^5$, $R^6$, $R^7$ and $R^8$ are as defined in formula (I), with a compound of general formula

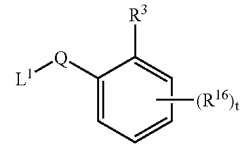
(V)

wherein $L^1$ represents a hydrogen atom or an activating group (e.g. Li when Q is $CH_2$) and Q, $R^3$, t and $R^{16}$ are as defined in formula (I); or (c) when $R^3$ represents —NHC(O)$R^{13}$, reacting a compound of general formula

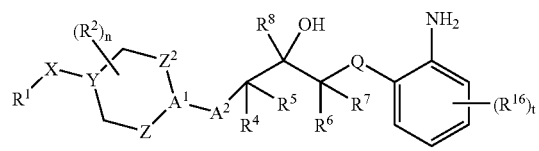
(VI)

wherein $R^1$, X, Y, n, $R^2$, $Z^1$, $Z^2$, $A^1$, $A^2$, Q, $R^4$, $R^5$, $R^6$, $R^7$, $R^8$, t and $R^{16}$ are as defined in formula (I), with a compound of general formula

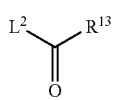
(VII)

wherein $L^2$ represents a leaving group (e.g. a hydroxyl group or a halogen atom such as chlorine) and $R^{13}$ is as defined in formula (I); or (d) when $R^3$ represents —C(O)$NR^{14}R^{15}$, reacting a compound of general formula

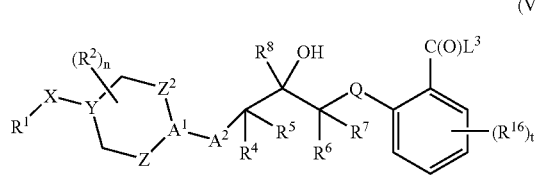
(VIII)

wherein $L^3$ represents a leaving group (e.g. a hydroxyl group or a halogen atom such as chlorine) and $R^1$, X, Y, n, $R^2$, $Z^1$, $Z^2$, $A^1$, $A^2$, Q, $R^4$, $R^5$, $R^6$, $R^7$, $R^8$, t and $R^{16}$ are as defined in formula (I), with a compound of general formula (IX), $NHR^{14}R^{15}$, wherein $R^{14}$ and $R^{15}$ are as defined in formula (I);

and optionally after (a), (b), (c) or (d) forming a pharmaceutically acceptable salt or solvate of the compound of formula (I) obtained.

The processes of the invention may conveniently be carried out in a solvent, e.g. an organic solvent such as an alcohol (e.g. methanol or ethanol), a hydrocarbon (e.g. toluene) or tetrahydrofuran or acetonitrile at a temperature of, for example, 0° C. or above such as a temperature in the range from 0, 5, 10, 15 or 20° C. to 100, 110 or 120° C.

Compounds of formulae (II), (II'), (III), (IV), (V), (VI), (VII), (VIII) and (IX) are either commercially available, are well known in the literature or may be prepared easily using known techniques.

It will be appreciated by those skilled in the art that in the process of the present invention certain fuinctional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of for- mula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemoldne receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, SJorgren's syndrome and systemic sclerosis;

(3) (skin) psoriasis, atopical dermatitis, contact dermatitis and other eczematous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels; and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease which comprises administering to a patient in need thereof a therapeutically effective amount of a compound of formula (I), or a pharmaceutically acceptable salt or solvate thereof, as hereinbefore defined.

The invention still further provides a method of treating an airways disease which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (er cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention flrter provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e g. by oral admi,istration in the form of tablets, capsules, syrups, powders or granules; or by parenteral administration in the form of solutions or suspensions; or by subcutaneous administration; or by rectal administration in the form of suppositories; or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm) were used as internal standard. Low resolution mass spectra and accurate mass determination were recorded on a Hewlett-Packard 1100 LC-MS system equipped with APCI/ESI ionization chambers. All solvents and commercial reagents were laboratory grade and used as received. The nomenclature used for the compounds was generated with ACD/IUPAC Name Pro.

STARTING MATERIALS FOR EXAMPLES 1-16

Pyrrolidines

A) 5-Chloro-2-(3-pyrrolidinyloxy) pyridine

To a stirred solution of 5-chloro-2-pyridinol (323.9 mg; 2.5 mmol), tert-butyl 3-hydroxy-1-pyrrolidinecarboxylate (468.0 mg, 2.5 mmol) and triphenylphosphine polymer bound (1 g, 3 mmol) in THF/CH$_2$Cl$_2$ (1:1, 5 ml) slowly was added diethyl azodicarboxylate (435.5 mg 2.5 mmol). The solution was slowly stirred overnight Resin was then removed by filtration and washed with THF. The combined filtrates were evaporated to dryness. The resulting residue was purified by RP-HPLC (10-40% CH$_3$CN). The pure material was treated with 95% TFA/5% H$_2$O, 30 min. The TFA phase was then evaporated to give the desired product as a solid.

APCI-MS: m/z 199.1 [M$^+$H$^+$]

$^1$H-NMR(400 MHz, CDCl$_3$): δ 8.06(d, 1H), 7.57(m, 1H), 6.72(d, 1H), 5.60(m, 1H), 3.63(m, 1H), 3.50(m, 3H), 2.32 (m, 2H)

B) 5-Bromo-2-(3-pyrrolidinyloxy)pyridine

The title compound was prepared from of 5-bromo-2-pyridinol (435 mg; 2.5 mmol), by a process analogous to that described in A) above.

APCI-MS: m/z 243.2 [M$^+$H$^+$]

$^1$H-NMR (400 MHz, CDCl$_3$): δ 7.98(m, 1H), 7.54(m, 1H), 7.36(m, 1H), 5.3(m, 1H), 3.62(m, 4H), 2.35(m, 2H).

C) 4-Methyl-2-(3-pyrrolidinyloxy)pyridine

The title compound was prepared from 4-methyl-2-pyridinol (273.0 mg; 2.5 mmol), by a process analogous to that described in A) above.

APCI-MS: m/z 179.2 [M$^+$H$^+$]

$^1$H-NMR (400 MHz, CDCl$_3$): δ 8.10(d, 1H), 7.06(m, 2H), 5.62(m, 1H), 3.64(m, 2H), 3.52(m, 2H), 2.42(s, 3H), 2.40(m, 2H).

D) 2-Chloro-6-(3-pyrrolidinyloxy) pyridine

The title compound was prepared from 2-chloro-6-pyridinol by a process analogous to that described in A) above.

$^1$H-NMR (400 MHz, CDCl$_3$): δ 7.50(m, 1H), 6.87(d, 1H), 6.63(d, 1H), 5.47(m, 1H), 3.17(m, 1H), 3.13(m, 2H), 2.93 (m, 1H), 2.15(m, 1H), 1,93(m, 1H).

Epoxides

E) N-[2-Fluoro-6-(2-oxiranylmethoxy)phenyl]acetamide
  i) 2-Amino-3-fluorophenol To a stirred solution of 2,6-difluoronitrobenzene (1100 mg, 6.9 mmol) in dry methanol (20 ml) was added a solution of sodium (180 mg, 7.8 mmol ) in dry methanol (8 ml). The solution was stirred overnight. After concentration water was added and the solution was extracted with ether, dried over MgSO$_4$, filtered and concentrated to a yellow residue (870 mg.5.08 mmol). To the solution of the yellow residue in dichloromethane (10 ml) was added boron tribromide (1M in dichloromethane, 10 ml) and stirred at room temperature overnight. Water was then added and the solution stirred for further 60 min. The organic phase was separated and the water phase was extracted with ether. The combined organic phases were dried over MgSO$_4$, filtered and concentrated in vacuo to give a brownish residue. The residue was taken up into ether and washed with 2M sodium hydroxide and water. The water and sodium hydroxide washings were combined and neutralized with 6M HCl and extracted with ether, dried over MgSO$_4$ and evaporated to give a yellow residue which was purified by flash chromatography on silica gel with EtOAc:Heptane; 1:3 as eluant to give the product (720 mg, 4.6 mmol) which was directly suspended with palladium-charcoal (140 mg) in water-ethanol (30 ml). Sodium borohydride (530 mg) was added over a period of 5 minutes and the suspension was stired at room temperature (1 h). The catalyst was removed by filtration through a Celite pad The filtrate was acidified with 6M hydrochloric acid to destroy any residual borohydride, neutralized with 2M sodium hydroxide, and then extracted with ether. The ethereal extracts were dried over MgSO$_4$ and evaporated.

APCI-MS: m/z 128.2 [M$^+$H$^+$]

ii) N-[2-Fluoro-6-(2-oxiranylmethoxy)phenyl]acetamide

To a stirred solution of 2-amino-3-fluorophenol (300 mg, 2.36 mmol) in water-methanol (10 ml) acetic acid anhydride was added until all 2-amino-3-fluorophenol was used. The solution was then concentrated to a residue of N-(2-fluoro-6-tiydroxyphenyl) acetamide. To a mixture of N-(2-fluoro-6-hydroxyphenyl) acetamide (399 mg, 2.36 mmol) and potassium carbonate (652 mg, 4.72 mmol) in DMF (5 ml) was added epibromohydrin (388 mg, 2.8 mmol) and was stirred at 70° C. for 3 hrs. Water and ethyl acetate were added. the organic phase separated, dried and concentrated. The resulting residue was purified by RP-HPLC (10-40% CH$_3$CN ) to give the desired product as a solid (242 mg, 1.08 mmol).

APCI-MS: m/z 226.2 [M$^+$H$^+$]

$^1$H-NMR (400 MHz, CDCl$_3$): δ 7.15(m, 1H), 6.80(m, 2H), 6.70(d, 1H), 4.3(m, 1H), 3.95(m, 1H), 3.3(m, 1H), 2.90(m, 1H), 2.75(m, 1H), 2.50(m, 1H), 2.20(s, 3H)

F) 3,5-Dimethyl-1H-pyrrole-2-carboxylic acid (2-oxiranylmethoxy-phenyl)-acetamide i) 3,5-Dimethyl-1H-pyrrole-2-carboxylic acid To a solution of ethyl 3,5-dimethyl-2-pyrrolecarboxylate (Aldrich) (504 mg, 3 mmol) in THF/H$_2$O/MeOH (5:1:1, 30 ml ) was added NaOH (480 mg, 12 mmol) in H$_2$O (12 ml). The mixture was stirred at 75° C. overnight. The homogeneous mixture was washed with ether. To the aqueous layer was added a saturated aqeos KHSO$_4$ solution until the pH was about 3. The solution was then extracted with dichloromethane. The extracts were dried over MgSO$_4$ and evaporated. The residue was purified on silica (ethylacetate/methanol, 90/10) to give the title compound (375 mg, 90%).

$^1$H-NMR (400 MHz, CDCl$_3$): δ 8.75(s, 1H), 5.83(s, 1H), 2.25(s, 1H), 2.38(s, 1H).

ii) 3,5-Dimethyl-1H-pyrrole-2-carboxylic acid (2-phenol)-acetamide

2-Aminophenol (545 mg 5 mmol), 3,5-dimethyl-1H-pyrrole-2-carboxylic acid (695 mg, 5 mmol) and HATU (1900 mg, 5 mmol) were stirred in DMF (20 ml). Diisopropylethylamine was added to pH 8. The mixture was stirred overnight and then concentrated. The residue was purified on RP-HPLC (acetonitrile/water, 10/90 to 40/60 with 0.5% trifluoroacetic acid) to give the title compound (550 mg, 48%).

APCI-MS: m/z 231.2 [M$^+$H$^+$]

$^1$H-NMR (400 MHz CDCl$_3$): δ 9.22(s, 1H); 7.63(s, 1H), 7.11(m, 2H), 7.03 (m, 1H), 6.88(m, 1H), 5.88(s, 1H), 2.44(s, 1H), 2.24 (s, 1H).

iii) 3,5-Dimethyl-1H-pyrrole-2-carboxylic acid (2-oxiranylmethoxy-phenyl)-acetamide The title compound was prepared from 3,5-dimethyl-1H-pyrrole-2-carboxylic acid (2-phenol)-acetamide (ii) (300 mg, 1.3 mmol) by a process analogous to that described in E ii) above.

APCI-MS: m/z 273.2 [M$^+$H$^+$]

$^1$H-NMR (400 MHz, CDCl$_3$): δ 8.46(m, 1H), 8.31(m, 1H), 6;99(m, 2H), 6.87(m, 1H), 5.85(m, 1H), 4.34(m, 1H), 3.92(m, 1H), 3.36(m, 1H), 2.91(m, 2H), 2.71 (m, 1H), 2.47(m, 3H), 2.25(m, 3H)

G) N-[2-(2-Oxiranylmethoxy) phenyl]benzamide

To a strred solution of N-(2-hydroxy-phenyl)-benzamide (0.81 g, 3.80 mmol), and cesium carbonate (1.61 g, 4.94 mmol) in acetonitrile was added epibromohydrin (0.63 ml, 7.60 mmol). After 4 hours the reaction mixture was partitioned between dichloromethane and water. After evaporation of the organic solvent, the residue was crystallized from petroleum ether and diethyl ether yielding the title compound (0.741 g, 73%).

APCI-MS: m/z 227 [M$^+$H$^+$]

$^1$H-NMR (400 MHz, CDCl$_3$): δ 8.65 (bs, 1H), 8.55 (bs, 1H), 7.94(d, 2H), 7.53(m, 3H), 7.08 (bs, 2H), 6.96 (bs, 1H), 4.42(d, IH), 4.02, (m, IH), 3.41 (bs, 1H), 2.96(s, 1H), (s, 1H).

H) N-4-Fluoro-2-[(2S) oxiranylmethoxy]phenyl)acetamide (2S)-2-[(5-Fluoro-2-nitrophenoxy)methyl]oxirane (0.32 g, 1.5 mmol) was dissolved in ethyl acetate (40 ml). Platinum on charcoal (0.15 g) was added, and the mixture was stirred in the atmosphere of hydrogen for 3 hours at room temperature ard atmospheric pressure. The catalyst was filtered and washed on the filter with ethyl acetate (10 ml). Acetic anhydride (0.31 g, 0.28 ml, 3 mmol) and ethyl di(isopropyl)amine (0.39 g, 0.52 ml, 3 mmol) were added to the solution. The reaction mixture was stirred at room temperature for 3 hours, then washed with 1M NaOH (30 ml) and brine (30 ml), and dried with Na$_2$SO$_4$. Evaporation of the solvent and flash chromatography on silica gel with n-heptane/ethyl acetate (from 25 to 75%) afforded the titled compound (0.21 g, 0.92 mmol, 61%) as a colourless solid product.

APCI-MS: m/z 226 [M$^+$H$^+$]

$^1$H-NMR (400 MHz, CDCl$_3$): δ 8.30 (dd, 1H, J=5.2, J=9.0), 7.71 (br. S, 1H), 8.6-8.8 (m, 2H), 436 (dd, 1H, J=2.3, J=11.3), 3.90 (dd, 1H, J=6.3, J=11.3), 3.40(m, 1H), 2.97 (t, 1H, J=4.4), 2.78 (dd, 1H, J=2.7, J=4.8), 2.21(s, 3H).

I) N-(4-Fluoro-2-1(2R) oxiranylmethoxy]phenyl)acetamide

The title compound was prepared from (2R)-2-[(5-fluoro-2-nitrophenoxy)methyl]oxirane according to the method described in H) above.

EXAMPLE 1

N-[2-(3-(3-[(5-Chloro-2-pyridinyl)oxy]-1-pyrrolidinyl)-2-hydroxypropoxy) phenyl]benzamide A solution of 5-chloro-2-(3-pyrrolidinyloxy) pyridine (100 μL, 0.2M/DMSO), N-[2-(2-oxiranylmethoxy)phenyl]benzamide (100 μL, 0.2 M/DMSO) was refluxed for 3 h.

APCI-MS: m/z 468.4 [M$^+$H$^+$]

The compounds of Examples 2 to 16 were prepared from the appropriate starting materials described above by processes analogous to that of Example 1 above.

EXAMPLE 2

N-[2-3-{3-[(5-Chloro-2-pyridinyl)oxy)]-1-pyrrolidinyl)-}2-hydroxypropoxy}-6-fluorophenyl)acetamide APCI-MS: m/z 424.3 [M$^+$H$^+$]

EXAMPLE 3

N-[2-(3-(3-[(5-Chloro-2-pyridinyl)oxy]-1-pyrrolidinyl)-2-hydroxypropoxy)-phenyl]acetamide APCI-MS: m/z 406.3 [M$^+$H$^+$]

EXAMPLE 4

N-[2-[(2S)-3-(3-[(5-Chloro-2-pyridinyl)oxy]-1-pyrrolidinyl)-2-hydroxypropoxy) -4-fluorophenyl]acetamide APCI-MS: m/z 424.3 [M$^+$H$^+$]

EXAMPLE 5

N-[2-[(2R)-3-(3-[(5-Chloro-2-pyridinyl)oxy]-1-pyrrolidinyl)-2-hydroxrypropoxy) -4-fluorophenyl]acetamide APCI-MS: m/z 424.3 [M$^+$H$^+$]

EXAMPLE 6

N-[2-(3-(3-[(5-Chloro-2-pyridinyl)oxy]-1-pyrrolidinyl)-2-hydroxypropoxy)-phenyl]3,5 -dimethyl-1-H-pyrrole-2-carboxyamide APCI-MS: m/z 485.4 [M$^+$H$^+$]

EXAMPLE 7

N-[2-3-(3-[(6-Chloro-2-pyridinyl)oxy]-1-pyrrolidinyl)-2-hydroxypropoxy) phenyl]benzamide APCI-MS: m/z 468.4 [M$^+$H$^+$]

EXAMPLE 8

N-[2-[(2S)-3-(3-[(6-Chloro-2-pyridinyl)oxy]-1-pyrrolidinyl)-2-hydroxypropoxy)-4-fluorophenyl] acetamide APCI-MS: m/z 424.3 M$^+$H$^+$]

EXAMPLE 9

N-[2-(3(3-[(5-Bromo-2-pyridinyl)oxy]-1-pyrrolidinyl)-2-hydroxypropoxy)phenyl]benzamide APCI-MS: m/z 512.3 [M$^+$H$^+$]

EXAMPLE 10

N-[2-(3(3-[(5-Bromo-2-pyridinyl)oxy]-1-pyrrolidinyl)-2-hydroxypropoxy)-6-fluorophenyl ]acetamide APCI-MS: m/z 468.3 [M$^+$H$^+$]

EXAMPLE 11

N-[2-(3-(3-[(5-Bromo-2-pyridinyl)oxy]-1-pyrrolidinyl)-2-hydroxypropoxy)phenyl]acetamide APCI-MS: m/z 450.3 [M$^+$H$^+$]

EXAMPLE 12

N-[2-[(2S)-3-(3-[(5-Bromo-2-pyridinyl)oxy]-1-pyrrolidinyl)-2-hydroxypropoxy)-4-fluorophenyl]acetamide APCI-MS: m/z 468.3 [M$^+$H$^+$]

EXAMPLE 13

N-[2-[(2R)-3-(3-[(5Bromo-2-pyridinyl)oxy]-1-pyrrolidinyl)-2-hydroxypropoxy)-4-fluorophenyl] acetamide APCI-MS: m/z 468.3 [M$^+$H$^+$]

EXAMPLE 14

N-[2-(3-3-[(5-Bromo-2-pyridinyl)oxy]-1-pyrroldinyl)-2-hydroxypropoxy)phenyl-]3,5-dimethyl-1H-pyrrole-2-carboxyamide APCI-MS: m/z 529.4 [M$^+$H$^+$]

EXAMPLE 15

N-[2-(2-Hydroxy-3-{3-[(4-methyl-2-pyridinyl)oxy]-1-pyrrolidinyl}propoxy) phenylbenzamide APCI-MS: m/z 448.4 [M$^+$H$^+$]

EXAMPLE 16

N-{4-Fluoro-2-[((2S)2-hydroxy-3-{3-[(4methyl-2-pyridinyl)oxy]-pyrrolidinyl}propyl)oxy] phenyl}acetamide APCI-MS: m/z 404.4 [M$^+$H$^+$]

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutarnax but without antibiotics. Optimal growth of the cells requires that they are passaged every 3 days and that the minimum subculture density is 4×10+5 cells/ml.

Chemotaxis Assay

Cells were removed from the flask and washed by centrifgation in RPMI+10% HIFCS+glutamax. The cells were then resuspended at 2×10+7 cells/ml in fresh medium (RPMI+10% HIFCS+glutamax) to which was added calcein-AM (5 μl of stock solution to 1 ml to give a final concentration of 5×10$^{-6}$ M). After gentle mixing the cells were incubated at 37° C. in a $CO_2$ incubator for 30 minutes. The cells were then diluted to 50 ml with medium and washed twice by centrifugation at 400×g. Labelled cells were then resuspended at a cell concentration of ×10+7 cells/nl and incubated with an equal volume of MIP-1α antagonist (10$^{-10}$ M to 10$^{-6}$ M final concentration) for 30 minutes at 37° C. in a humidified $CO_2$ incubator.

Chemotaxis was performed using Neuroprobe 96-well chemotaxis plates employing 8 μm filters (cat no. 101-8). Thirty microlitres of chemoattractant supplemented with various concentrations of antagonists or vehicle were added to the lower wells of the plate in triplicate. The filter was then carefullly positioned on top and then 25 μl of cells preincubated with the corresponding concentration of antagonist or vehicle were added to the surface of the filter. The plate was then incubated for 2 hours at 37° C. in a humidified $CO_2$ incubator. The cells remaining on the surface were then removed by adsorption and the whole plate was centrifuged at 2000 rpm. for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

What is claimed is:

1. A compound of the following formula

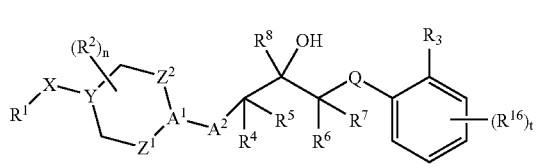

(I)

wherein $R^1$ represents 2-pyridinyl being optionally substituted by one or more substituents independently selected from halogen, cyano, nitro, carboxyl, hydroxyl, $C_1$-$C_6$ alkyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^9R^{10}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido, $C_1$-$C_6$ alkylsuiphonyl and —$C(O)NR^{11}$ $R^{12}$;

X represents an oxygen or sulphur atom and Y represents a CH or C(OH) group;

n is 0, 1 or 2;

each $R^2$ independently represents a $C_1$-$C_6$ alkyl, $C_1$-$C_6$ alkoxycarbonyl, —$CH_2OH$ or carboxyl group;

$Z^1$ represents a bond or a group $CH_2$;

$Z^2$ represents a bond or a group $CH_2$, with the proviso that $Z^1$ and $Z^2$ do not both simultaneously represent a bond or $CH_2$;

$A^1$ represents a nitrogen atom and $A^2$ represents a bond;

Q represents an oxygen or sulphur atom or a group $CH_2$ or NH;

$R^3$ represents —$NHC(O)R^{13}$ or —$C(O)NR^{14}$ $R^{15}$;

$R^4$, $R^5$, $R^6$ and $R^7$ each independently represent a hydrogen atom or a $C_1$-$C_6$ alkyl group, or $R^4$, $R^5$, $R^6$ and $R^7$ together represent a $C_1$-$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$-$C_6$ alkyl group or is linked to $R^4$ as defined above;

$R^9$ and $R^{10}$ each independently represent a hydrogen atom or a $C_1$-$C_6$ alkyl group;

$R^{11}$ and $R^{12}$ each independently represent a hydrogen atom or a $C_1$-$C_6$ alkyl group;

$R^{13}$ represents a group $C_1$-$C_6$ alkyl, $C_2$-$C_6$ alkenyl, $C_3$-$C_6$ cycloalkyl, adamantyl, $C_5$-$C_6$ cycloalkenyl, or phenyl, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{17}$;

$R^{14}$ and $R^{15}$ each independently represent (i) a hydrogen atom, (ii) a 5- to 6-membered saturated or unsaturated cycloalkyl or phenyl ring optionally substituted with at least one substituent selected from halogen, methyl and trifluoromethyl, or (iii) a $C_1$-$C_6$ alkyl group optionally substituted by at least one substituent selected from halogen, trifluoromethyl, carboxyl, $C_1$-$C_6$ alkoxycarbonyl and a 5- to 6-membered saturated or unsaturated cycloalkyl or phenyl ring optionally substituted with at least one substituent selected from halogen, methyl and trifluoromethyl;

t is 0, 1, 2 or 3;

each $R^{16}$ independently represents halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ haloalkyl, $C_1$-$C_6$ haloalkoxy, —$NR^{18}$ $R^{19}$, $C_3$-$C_6$ cycloalkylamino, $C_1$-$C_6$ alkylthio, $C_1$-$C_6$ alkylcarbonyl, $C_1$-$C_6$ alkylcarbonylamino, sulphonamido (—$SO_2NH_2$), $C_1$-$C_6$ alkylsulphonyl, —$C(O)NR^{20}$ $R^{21}$, —$NR^{22}$ $C(O)(NH)_x R^{23}$, phenyl, or $C_1$-$C_6$ alkyl optionally substituted by at least one substituent selected from carboxyl and $C_1$-$C_6$ alkoxycarbonyl;

$R^{17}$ represents a $C_1$-$C_6$ alkyl, amino (—$NH_2$) or phenyl group;

$R^{18}$ and $R^{19}$ each independently represent a hydrogen atom or a $C_1$-$C_6$ alkyl group;

$R^{20}$ and $R^{21}$ each independently represent a hydrogen atom or a $C_1$-$C_6$ alkyl group optionally substituted by $C_1$-$C_6$ alkoxycarbonyl;

v is 0 or 1;

$R^{22}$ represents a hydrogen atom or a $C_1$-$C_6$ alkyl group; and $R^{23}$ represents a hydrogen atom, or a $C_1$-$C_6$ alkyl group optionally substituted by at least one substituent selected from carboxyl, $C_1$-$C_6$ alkoxy and $C_1$-$C_6$ alkoxycarbonyl; or a pharmaceutically acceptable salt thereof.

2. A compound according to claim 1, wherein X represents O.

3. A compound according to claim 1, wherein Y represents a CH group.

4. A compound according to claim 1, wherein Q represents an oxygen atom.

5. A compound according to claim 1, wherein $R^3$ represents —NHC(O)$R^{13}$ and $R^{13}$ represents $C_1$-$C_6$ alkyl, or phenyl, each of which mat be optionally substituted by one, two, three or four substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)-$R^{17}$.

6. A compound according to claim 1 being:

N-[2-(3-(3-[(5Chloro-2-pyridinyl)oxy]-1-pyrrolidinyl)-2-hydroxypropoxy) phenyl]benzamide, or N-[2-(3- {3-[(5-Chloro-2-pyridinyl)oxy)]-1-pyrrolidinyl}-2-hydroxypropoxy}-6-fluorophenyl)acetamide, or N-[2-(3-(3-[(5-Chloro-2-pyridinyl)oxy]-1-pyrrolidinyl)-2-hydroxypropoxy)-4-fluorophenyl]acetamide, or N-[2-[(2S)-3-(3-[(5-Chloro-2-pyridinyl)oxy]-1-pyrrolidinyl)-2-hydroxypropoxy)-4-fluorophenyl]acetamide, or N-[2-[(2R)-3-(3-[(5-Chloro-2-pyridinyl)oxy]-1-pyrrolidinyl)-2-hydroxypropoxy)-4-fluorophenyl]acetamide, or N-[2-(3-(3-[(6-Chloro-2-pyridinyl)oxy]-1-pyrrolidinyl)-2-hydroxypropoxy) phenyl]benzamide, or N-[2-[(2S)-3-(3-[(6-Chloro-2-pyridinyl)oxy]-1-pyrrolidinyl)-2-hydroxypropoxy)-4-fluorophenyl]acetamide, or N-[2-(3-(3-[(5-Bromo-2-pyridinyl)oxy]-1-pyrrolidinyl)-2-hydroxypropoxy)phenyl]benzamide, or N-[2-(3-(3-[(5-Bromo-2-pyridinyl)oxy]-1-pyrrolidinyl)-2-hydroxypropoxy)-6-fluorophenyl]acetamide, or N-[2-(3-(3-[(5-Bromo-2-pyridinyl)oxy]-1-pyrrolidinyl)-2-hydroxypropoxy)phenyl]acetamide, or N-[2-[(2S)-3-(3-[(5-Bromo-2-pyridinyl)oxy]-1-pyrrolidinyl)-2-hydroxypropoxy)-4-fluorophenyl]acetamide, or N-[2-[(2R)-3-(3-[(5-Bromo-2-pyridinyl)oxy]-1-pyrrolidinyl)-2-hydroxypropoxy)-4-fluorophenyl]acetamide, or N-[2-(2-Hydroxy-3-{3-[(4-methyl-2-pyridinyl)oxy]-1-pyrrolidinyl}propoxy) phenylbenzamide, or N-{4-Fluoro-2-[((2S)2-hydroxy-3-{3-[(4-methyl-2-pyridinyl)oxy]-1-pyrrolidinyl}propyl)oxy] phenyl}acetamide.

7. A process for the preparation of a compound of formula (I) as defined in claim 1 which comprises, (a) reacting either a compound of formula

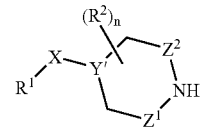
(II)

wherein Y' represents CH or C(OH) and $R^1$, X, n, $R^2$, $Z^1$ and $Z^2$ are as defined in formula (I), or a compound of the following formula

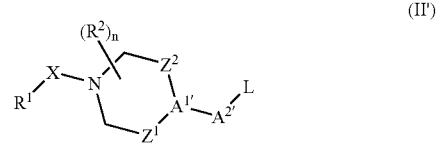
(II')

wherein $A^{1'}$ represents a nitrogen atom and $A^{2'}$ represents $CH_2$ or a bond, L represents a hydrogen atom or a lithium ion and $R^1$, X, n, $R^2$, $Z^1$ and $Z^2$ are as defined in formula (I), with a compound of the following formula

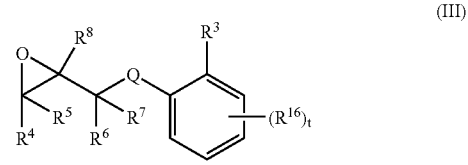
(III)

wherein Q, $R^3$, $R^4$, $R^5$, $R^6$, $R^7$, $R^8$, t and $R^{16}$ are as defined in formula (I); or (b) reacting a compound of the following formula

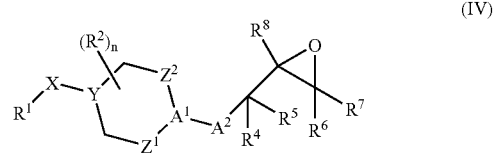
(IV)

wherein $R^1$, X, Y, n, $R^2$, $Z^1$, $Z^2$, $A^1$, $A^2$, $R^4$, $R^5$, $R^6$, $R^7$ and $R^8$ areas defined in formula (I), with a compound of the following formula

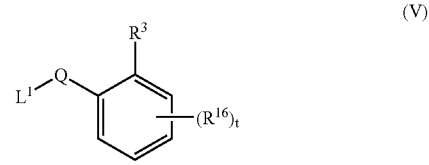
(V)

wherein $L^1$ represents a hydrogen atom or a lithium ion and Q, $R^3$, t and $R^{16}$ are as defined in formula (I); or (c) when $R^3$ represents —NHC(O)$R^{13}$, reacting a compound of the following formula

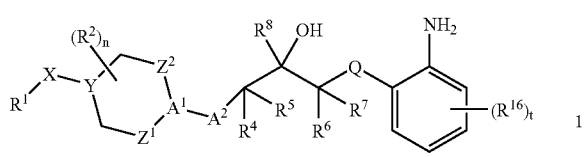

(VI)

wherein $R^1$, X, Y, n, $R^2$, $Z^1$, $Z^2$, $A^1$, $A^2$, Q, $R^4$, $R^5$, $R^6$, $R^7$, $R^8$, t and $R^{16}$ areas defined in formula (I), with a compound of the following formula

(VII)

wherein $L^2$ represents a leaving group and $R^{13}$ is as defined in formula (I); or (d) when $R^3$ represents —C(O)NR$^{14}$R$^{15}$, reacting a compound of the following formula

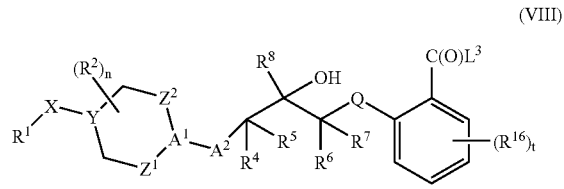

(VIII)

wherein $L^3$ represents a leaving group and $R^1$, X, Y, n, $R^2$, $Z^1$, $Z^2$, $A^1$, $A^2$, Q, $R^4$, $R^5$, $R^6$, $R^7$, $R^8$, t and $R^{16}$ are as defined in formula (I), with a compound of general formula (IX), NHR$^{14}$R$^{15}$, wherein $R^{14}$ and $R^{15}$ are as defined in formula (I);

and optionally after (a), (b), (c) or (d) forming a pharmaceutically acceptable salt of the compound of formula (I) obtained.

8. A pharmaceutical composition comprising a compound of formula (I), or a pharmaceutically acceptable salt thereof, as claimed in claim 1 association with a pharmaceutically acceptable adjuvant, diluent or carrier.

* * * * *

UNITED STATES PATENT AND TRADEMARK OFFICE
CERTIFICATE OF CORRECTION

PATENT NO. : 7,345,063 B2
APPLICATION NO. : 10/472017
DATED : March 18, 2008
INVENTOR(S) : Tomas Eriksson It is certified that error appears in the above-identified patent and that said Letters Patent is hereby corrected as shown below:

On the Title Page, Item (57), Pg. 1,
Abstract: After the word "therapy" insert -- . --

On the Title Page, Other Publications, Pg. 2,
Chou et al., Delete "polyarthritus" and replace with -- polyarthirtis --

On the Title Page, Other Publications, Pg. 2,
Eriksson et al., Delete "137:2476987" and replace with -- 137:247698 --

On the Title Page, Other Publications, Pg. 2,
Levine, Delete "109:25680" and replace with -- 109:52680 --

On the Title Page, Other Publications, Pg. 2,
Saeki, Delete "Moleclar" and replace with -- Molecular --

On the Title Page, Other Publications, Pg. 2,
Saeki, Delete "arthritus" (two instances) and replace with -- arthritis --

On the Title Page, Other Publications, Pg. 2,
Schmidt et l., Delete "et 1." and replace with -- et al. --

On the Title Page, Other Publications, Pg. 2,
Schmidt et al., Delete "mechanism" and replace with -- mechanisms --

Column 18
Line 4, Delete "alkylsuiphonyl" and replace with -- alkylsulphonyl --

Column 18
Line 56, Delete "$NR^{18} R^{19}$" and replace with -- $NR^{18}R^{19}$ --

Column 18
Line 59, Delete "$C(O)NR^{20} R^{21}$" and replace with -- $C(O)NR^{20}R^{21}$ --

UNITED STATES PATENT AND TRADEMARK OFFICE
CERTIFICATE OF CORRECTION

PATENT NO. : 7,345,063 B2
APPLICATION NO. : 10/472017
DATED : March 18, 2008
INVENTOR(S) : Tomas Eriksson It is certified that error appears in the above-identified patent and that said Letters Patent is hereby corrected as shown below:

Column 19
Claim 5, Line 2, After "represents" and before "$C_1$-$C_6$" insert -- a group --

Column 19
Claim 6, Line 4, Delete "N-[2-(3 {3-[(5-Chloro-2-pyridinyl)oxy]" and replace with -- N-[2-(3{3-[(5-Chloro-2-pyridinyl)oxy] --

Column 19
Claim 6, Line 8, Delete "4-fluorophenyl" and replace with -- phenyl --

Column 20
Line 54, Delete "areas" and replace with -- are as --

Column 21
Line 15, Delete "areas" and replace with -- are as --

Signed and Sealed this

Thirteenth Day of January, 2009

JON W. DUDAS
*Director of the United States Patent and Trademark Office*